US008001876B1

(12) United States Patent
Tabb et al.

(10) Patent No.: US 8,001,876 B1
(45) Date of Patent: Aug. 23, 2011

(54) BLOCK ALIGNMENT FOR MICROTOMES

(75) Inventors: Brian Carroll Tabb, Cumberland, MD (US); Keith Rogers, Singapore (SG)

(73) Assignee: SAIC-Frederick, Inc., Frederick, MD (US)

( * ) Notice: Subject to any disclaimer, the term of this patent is extended or adjusted under 35 U.S.C. 154(b) by 429 days.

(21) Appl. No.: 12/153,110

(22) Filed: May 14, 2008

(51) Int. Cl.
*B26D 7/01* (2006.01)
(52) U.S. Cl. ..... 83/522.15; 83/468; 83/915.5; 33/514.2; 33/561.1; 33/645
(58) Field of Classification Search ........... 83/13, 915.5, 83/467.1, 468, 468.1–468.4, 522.11, 522.15–522.19, 83/522.22–522.24; 33/640, 645, 568, 569, 33/265, 514.2, 561.1; 40/446, 427
See application file for complete search history.

(56) References Cited

U.S. PATENT DOCUMENTS

| 664,118 | A |   | 12/1900 | Becker |         |
|---------|---|---|---------|--------|---------|
| 2,523,647 | A | * | 9/1950 | Burk ............................ | 33/514.2 |
| 4,700,600 | A | * | 10/1987 | Pickett ........................... | 83/165 |
| 4,878,486 | A | * | 11/1989 | Slater ........................... | 600/186 |
| 5,082,254 | A |   | 1/1992 | Hunnell et al. ............... | 269/269 |
| 5,148,729 | A | * | 9/1992 | Krumdieck .................. | 83/411.1 |
| 5,161,446 | A | * | 11/1992 | Holbl et al. ..................... | 83/703 |
| 5,282,404 | A |   | 2/1994 | Leighton et al. .................. | 83/13 |
| 5,711,200 | A | * | 1/1998 | Thiem ............................. | 83/170 |
| 6,058,824 | A |   | 5/2000 | Neymeyr .................... | 83/698.21 |
| 6,160,264 | A | * | 12/2000 | Rebiere .................... | 250/559.22 |
| 7,066,067 | B2 |   | 6/2006 | Hess ................................ | 83/167 |
| 7,146,894 | B2 |   | 12/2006 | Hendrick et al. ............... | 83/703 |
| 2004/0020087 | A1 | * | 2/2004 | Fleming .......................... | 40/446 |
| 2004/0244548 | A1 | * | 12/2004 | Zimmermann et al. .......... | 83/13 |
| 2005/0147538 | A1 |   | 7/2005 | Williamson, IV et al. .... | 422/102 |
| 2005/0223862 | A1 | * | 10/2005 | Oberheim .................... | 83/477.2 |
| 2005/0279200 | A1 | * | 12/2005 | Duginske .................... | 83/471.3 |
| 2006/0219080 | A1 |   | 10/2006 | Heid ............................... | 83/651 |

OTHER PUBLICATIONS

"Clinical Laboratory Technologists and Technicians," Bureau of Labor Statistics, U.S. Department of Labor, *Occupational Outlook Handbook*, 2006-2007 Edition (accessed Dec. 15, 2006), http://www.bls.gov/oco/ocos096.htm.
Ellis, Roy, "Problems and 'Did You Know's' in Histophathological Technique," IHC World, originally accessed on Dec. 31, 2006 [retrieved on May 11, 2011], 4 pp., Retrieved From the Internet: http://www.ihcworld.com/royellis/Problems/index.html.
"Certification," American Society for Clinical Pathology, originally accessed on Dec. 14, 2006 [retrieved on May 11, 2011], 1 p., Retrieved From the Internet: http://www.ascp.org/certification/default.aspx.

(Continued)

*Primary Examiner* — Phong H Nguyen
(74) *Attorney, Agent, or Firm* — King & Spalding LLP

(57) ABSTRACT

Systems and methods described herein for aligning a block in a microtome attempt to save time, money, and the sample by aligning a block in any rotary or cryostat microtome. One such device for aligning a block in a microtome has a knife holder component removably attached to a knife holder of the microtome and a pin alignment component extending vertically from the knife holder component in a direction substantially parallel to the block. The pin alignment component has a plurality of front pins extending from a front surface of the pin alignment component configured to slide in response to an angle of the block and a plurality of rear pins extending from a rear surface of the pin alignment component and coupled to the front pins. The rear pins are configured to indicate the extension of the front pins from the pin alignment component.

11 Claims, 9 Drawing Sheets

OTHER PUBLICATIONS

"HM 340E," Microm International, [retrieved on May 11, 2011], 1 p., Retrieved From the Internet: http://www.microm.de/microm%20homepage.html/home_e.hmtl.

"LMT F14—A Laser Microtome For Precise, Non-Contact Sectioning," Rowiak-Products, Products, originally accessed on Dec. 12, 2006 [retrieved on May 11, 2011], 1 p., Retrieved From the Internet: http://.rowiak.com/products.htm.

"Histo Collimator," Microm International, originally accessed on Dec. 13, 2006 [retrieved on May 11, 2011], 1 p., Retrieved From the Internet: http://www.microm.de/Microm%20Homepage/html/histo_collimator_e.html.

Urban, Glen L. and von Hippel, Eric, "Lead User Analyses For the Development of New Industrial Products," Jun., 1986, 24 pp.

"Prostate Cancer Tests Might Miss One in Seven Cases," UniSci, originally accessed on Dec. 15, 1006 [retrieved on May 11, 2011], 2 pp., http://www.unisci.com/stories/20013/0709012.htm.

"Laboratory Ergonomics: Microtomy," Ergonomic Resources, originally accessed on Dec. 15, 2006 [retrieved on May 11, 2011], 6 pp., Retrieved From the Internet: http://www.dehs.umn.edu/ergo/lab/#microtomy.

American Society For Clinical Pathology, "About Us," originally accessed on Dec. 12, 2006 [retrieved on May 11, 2011], 1 p., Retrieved From the Internet: http://www.ascp.org/aboutus/default.aspx.

Gschwendtner, A. and Mairinger, T., "How Thick is Your Section? The Influence of Section Thickness on DNA-Cytometry on Histological Sections," *Analytical Cellular Pathology*, vol. 9, No. 1, Jul., 1995, 10 pp.

Gibbs, Hope J., "The Hidden Profession of Histotechnology," *Techniques*, Oct. 2004 [retrieved on May 18, 2011], 27 pp., Retrieved From the Internet: http://www.acteonline.org/content.aspx?id=5746.

"Cell/Tissue Culture Supplies," Global Industry Analysts, Oct. 1, 2010 [retrieved on May 12, 2011], 2 pp., Retrieved From the Internet: http://www.marketresearch. com/product/display. asp-?productid=2876767&SID=77738459.

"Re: [Histonet] Block Alignment," originally accessed on Dec. 13, 2006 [retrieved on May 12, 2011], 3 pp., Retrieved From the Internet: http;//www.histosearch.com/histonet/Mar05/RE.Histonetblockalignment.html.

Modern Pathology, "About the Journal," originally accessed on Dec. 12, 2006 [retrieved on May 12, 2011], 5 pp., Retrieved From the Internet: http://www.nature.com/modpathol/about.html.

Thermo Scientific, "About Us," originally accessed on Dec. 15, 2006 [retrieved on May 24, 2011], 1 p., Retrieved From the Internet: http;//www.thermo. com/com/cda/aboutus/home/0.1025_00.html.

"The Market For Tissue Microarrays," *Bioinformatics*, Jul. 2003 [retrieved on May 12, 2011], 3 pp., Retrieved From the Internet: http;//www.the-infoshop.com/report/fb14859_tissue_microarrays.html.

"Trends and Emerging Technologies in Drug Discovery," Dec. 29, 2005 [retrieved on May 12, 2011], 3 pp., Retrieved From the Internet: http://www.frost.com/prod/servlet/report-brochure.pag?id=F299-01-00-00-00.

"Repetitive Motion Disorders (RMD)—A Rapidly Increasing Problem For the Histoloty Laboratory of Tomorrow," originally accessed Dec. 15, 2006 [retrieved on May 24, 2011], 3 pp., Retrieved From the Internet: http://www.hbu.de/rmd.htm.

"NCI-Frederick" [online], retrieved on Jun. 6, 2011, 2 pp., Retrieved From the Internet: http://www.ncifcrf.gove.

\* cited by examiner

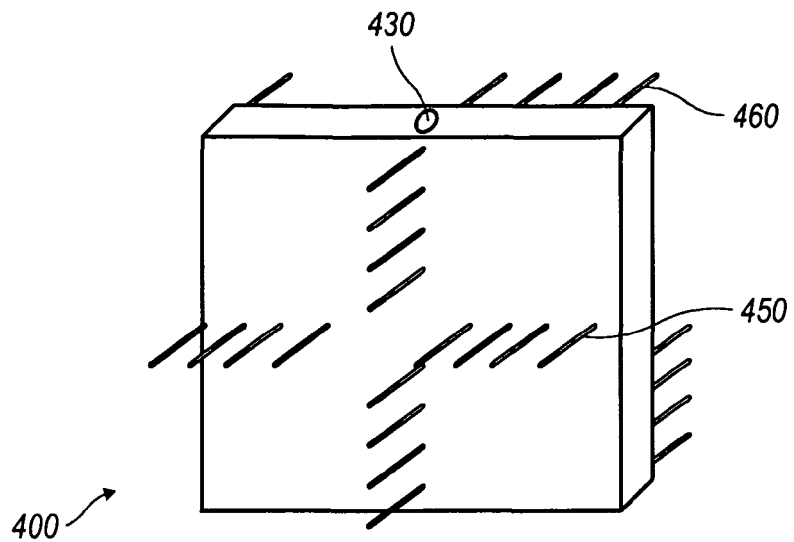
*FIG. 4a*
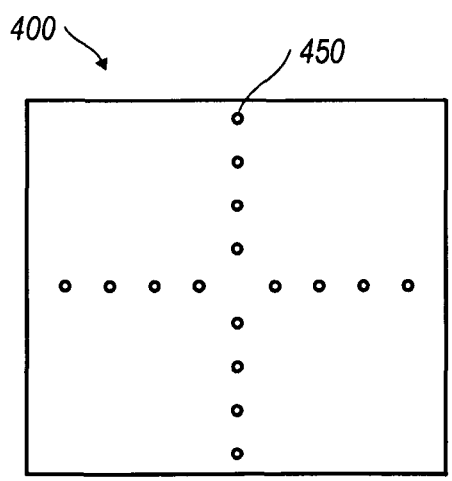 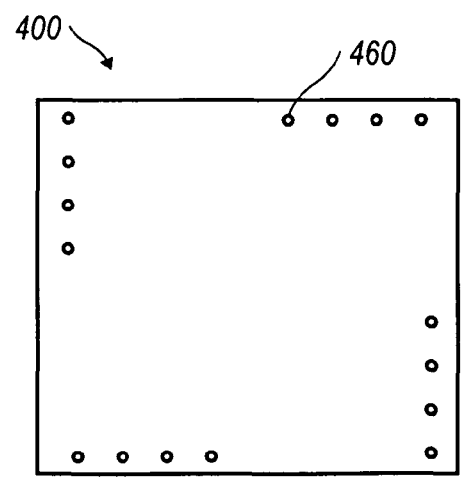
*FIG. 4b*            *FIG. 4c*

BLOCK ALIGNMENT FOR MICROTOMES

This invention was made with Government support under contract N01-CO-12400 awarded by the National Cancer Institute. The Government may have certain rights in the invention.

BACKGROUND OF THE INVENTION

1. Field of the Invention

The invention relates generally to systems and methods for aligning or realigning a block specimen in a microtome.

2. Background

Scientists and medical professionals often analyze tissue from humans, animals, or other biological specimens in a microscopic examination to diagnose various diseases and conditions. One method of preparing these specimens for histological examination is through the use of a rotary (also known as a table microtome) or cryostat microtome. Microtomes are mechanical devices used to consistently create thin sections, typically between 5 and 10 µm, of biological specimens. When cutting on a rotary microtome, harvested specimens reside in blocks of paraffin, whereas in cryostat microtomes, specimens are embedded in optimal cutting temperature (OCT) frozen media. In contrast to the rotary microtome, the cryostat microtome has a microtome unit mounted in a cooling enclosure with externally mounted controls. After the specimens are sliced in either type of microtome, the sliced sections can be stained and examined.

Generally, in operation of a rotary or cryostat microtome, the block having the specimen (referred to herein as a "block specimen") is secured to a chuck and clamped into the microtome. By fixing the chuck to the microtome, a user can align the block specimen along any of three planes (i.e., in X-, Y-, and Z-planes) in juxtaposition to a stationary thin knife (or blade). Once the block specimen is aligned with the knife, the user conducts a process known as "facing" or "truing" the block specimen.

During the truing process, the user operates a handwheel on the microtome to advance the block forward and vertically across the surface of the knife until complete sections of the block specimen are consistently sliced and the specimen itself is substantially exposed. Each rotation of the handwheel actuates mechanical gearing within the microtome to incrementally advance the block specimen forward for cutting the next (serial) section. Once the user obtains a desired sectioning surface and depth, the user can begin to slice sections for analysis. However, the conventional truing process has its limitations.

Slight misalignments of the block specimen to the knife or imperfections in the flatness of the block specimen's surface in juxtaposition to the knife can result in an incomplete section unsuitable for subsequent analysis. As slicing continues during the truing, incomplete sections or slices may contain specimen, as opposed to being entirely paraffin, and may be discarded. Furthermore, because many conventional microtomes allow the chuck to be adjusted in all three planes, it can be very challenging for sets of block specimens cut on a single microtome or for block specimens cut on different microtomes to have cutting planes that match in all three planes. For example, using a manual, time-consuming process, a user can attempt to align a block specimen by adjusting various angles of the chuck and then slicing a section with the knife to ascertain whether the block specimen's surface is substantially aligned with the cutting plane of the knife. This trial-and-error process is repeated until the user can slice a full section of the block. Moreover, microtomes are not designed to record the alignment angles by which a given block specimen resides within a chuck, so block specimens returning to a microtome for further slicing may require the user to conduct the time-consuming alignment process. Microtomes are also not engineered to automatically re-align the chuck to match the cutting planes of previously sectioned blocks, thereby requiring manual realignment by a user. As a result, the user may need to re-true the block each time it is positioned for slicing in a microtome. Manual realignment of the block can be very tedious and difficult. And sequential re-truing of blocks typically results in a substantial loss of sample before a complete section is properly sliced. Even those users who re-embed the entire block specimen or the specimen itself in a new block and then attempt to align the newly formed block specimen would similarly encounter these challenges.

Conventional attempts to align a block within a microtome are insufficient. For example, Microm's histo collimator attempts to align a block using a laser. In its general operation, the histo collimator uses a sight, a light source, and a mirror. The mirror is mounted on the surface of the block and reflects the light back to a crosshair in the sight. When a light beam from the light source is centered on the crosshair, the block is aligned in the horizontal and perpendicular planes. However, this equipment is very expensive and is operable on only Microm's microtomes. In another example of conventional equipment, such as those made by Newcomer Supply, Advanced Innovations, and Market Lab, a microtome aligner can set the microtome to zero in the X-, Y-, and Z-planes. If a plane is not set to zero, the block will not be properly aligned. For example, when using a block that was previously cut on a different microtome, the block aligned along a zero X-, Y-, and Z-plane of one microtome may not correlate to a zero X-, Y-, and Z-plane of another microtome. Additionally, a zero plane for a chuck holding a block does not necessarily correlate to a block surface perpendicular to the knife, so the block may require further alignment. This equipment is also expensive and is operable on only certain microtomes.

In addition to the disadvantages of the conventional equipment for aligning blocks in rotary microtomes, none of this conventional equipment is applicable to cryostat microtomes. Indeed, after over 100 years of advances in microtome technology, there still exists a need for accurately and consistently aligning and realigning block specimens in microtomes, as well as an alignment system or method that can be used on different types of microtomes.

SUMMARY OF THE INVENTION

Various embodiments described herein attempt to save time, money, and/or conserve the sample by aligning or realigning a block in any rotary or cryostat microtome, thereby eliminating or substantially reducing a need for aligning previously cut blocks. Embodiments of the systems and methods described herein can align tissue samples residing in a paraffin wax or OCT frozen media blocks in a substantially consistent three-dimensional orientation within a histological microtome or cryostat microtome prior to histological sectioning. As one potential benefit, the embodiments described herein may allow a user to more expediently and more accurately align and realign blocks in a microtome. As another potential benefit, the embodiments described herein may prolong the sharpness of a microtome knife, which needs to be periodically replaced or sharpened. These embodiments may prevent waste of specimens due to less truing. As a result, because less truing, and likely less training, may be required, specimens may be sliced more expediently, which can assist in preserving biological integrity.

In one exemplary embodiment, a device for aligning a block specimen in a microtome has a knife holder component removably attached to a knife holder of the microtome and a pin alignment component extending vertically from the knife holder component in a direction substantially parallel to the block specimen. The pin alignment component has a plurality of front pins extending from a front surface of the pin alignment component configured to slide in response to an angle of the block specimen and a plurality of rear pins extending from a rear surface of the pin alignment component and coupled to the front pins. The rear pins are configured to indicate the extension of the front pins from the pin alignment component.

In another exemplary embodiment, a method for aligning a block specimen in a microtome has the steps of attaching a pin alignment component to a microtome, wherein the pin alignment component comprises a plurality of pins, moving the block specimen in the microtome into a position to abut at least one of the plurality of pins, and re-positioning the block specimen in the microtome so that substantially all of the plurality of pins contact the block specimen at about the same distance from the pin alignment component.

In yet another exemplary embodiment, a microtome block specimen alignment component having a pin alignment component comprising a plurality of pins has a means for engaging the microtome block specimen, and a means for measuring the extent that the means for engaging has contacted the microtome block specimen.

Additional features and advantages of an embodiment will be set forth in the description which follows, and in part will be apparent from the description, or may be learned by practice of the invention. The objectives and other advantages of the invention will be realized and attained by the structure particularly pointed out in the exemplary embodiments in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The preferred embodiments of the present invention are illustrated by way of example and not limited to the following figures:

FIGS. 4a to 4c show views of a pin alignment component according to an exemplary embodiment;

DETAILED DESCRIPTION

Reference will now be made in detail to the preferred embodiments of the present invention, examples of which are illustrated in the accompanying drawings.

The various embodiments and configurations are not intended to be limited to any particular type of microtome or microtome model. In fact, many embodiments described herein are intended, although not required, to be interchangeable with various microtomes. In one example, the microtome can be a rotary microtome, such as the Leica Microsystems RM2255 rotary microtome, or a cryostat microtome, such as the Leica Microsystems CM3050S cryostat microtome. The embodiments can be configured for use in a rotary or cryostat microtome with minimal variation, including the use of materials suitable for room temperature or a cooler environment. In another example, the microtome can be a slide microtome or a disk/saw microtome, as well as an automated microtome. Thus, although the exemplary embodiments illustrate a rotary microtome, it is not intended to be limited to that particular microtome.

Figure 1:
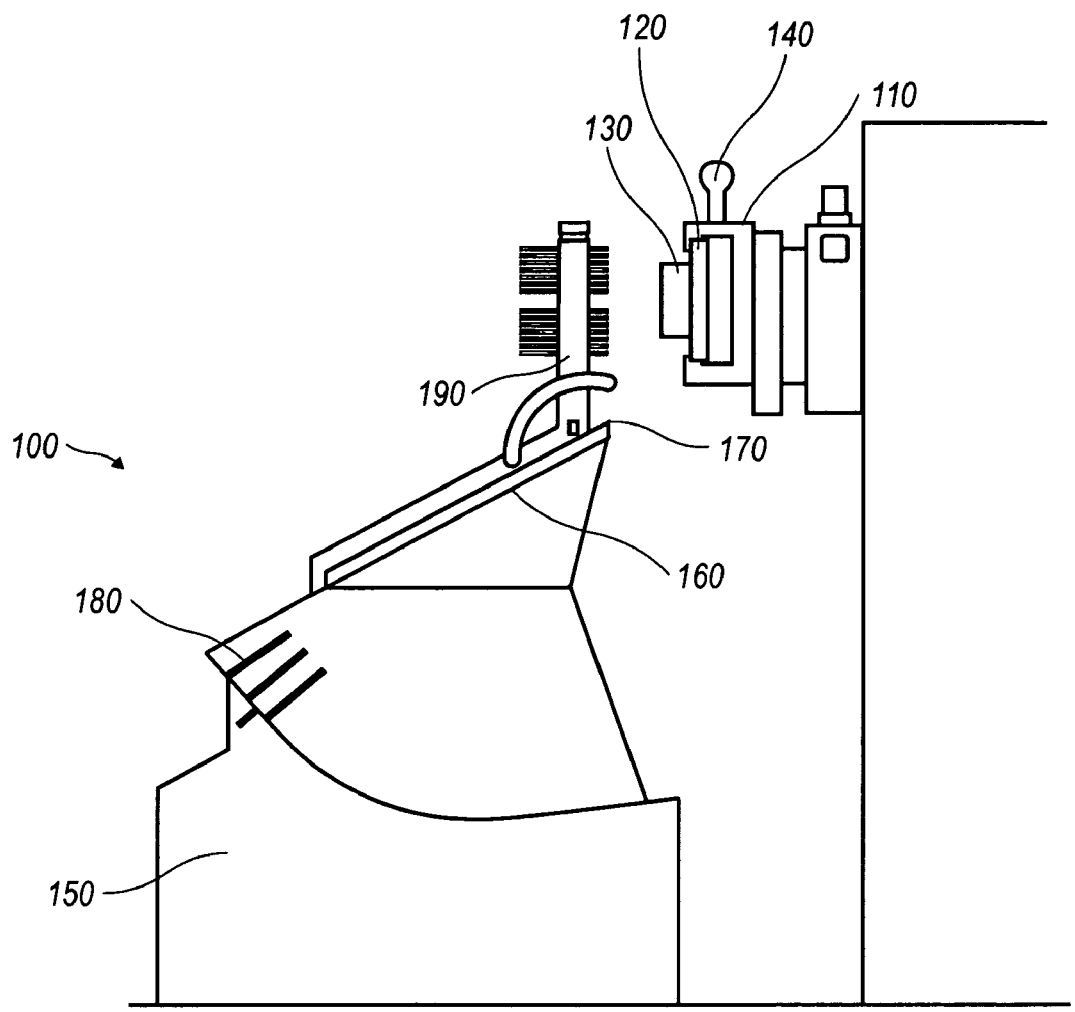
FIG. 1 shows a side view of a microtome with an alignment component according to an exemplary embodiment.

Referring to FIG. 1, a side view of a conventional rotary microtome 100 having an exemplary alignment device 190 is shown. In order to secure a block specimen 130, microtome 100 has a block clamp 110 having a block cartridge or chuck 120 that holds the block specimen, e.g., paraffin or OCT block, 130. A clamp adjustment knob 140 can be used to secure the chuck 120 and block specimen 130.

In order to slice the block specimen 130, a knife holder base 150 has a knife holder 160 and a knife blade 170. The angle of the knife holder 160 and the knife blade 170 can be adjusted using a clearance angle adjustment 180. According to one embodiment, the alignment device 190 is positioned on the knife holder 160, and can be attached using magnetism, a clamp, screws or bolts, or any other attachment mechanism known to one of ordinary skill in the art. As described in further detail herein, the alignment device 190 can assist a user in aligning the block specimen 130 at an optimal angle for slicing. The alignment device 190 according to this exemplary embodiment is shown in more detail in FIG. 2.

Figure 2:
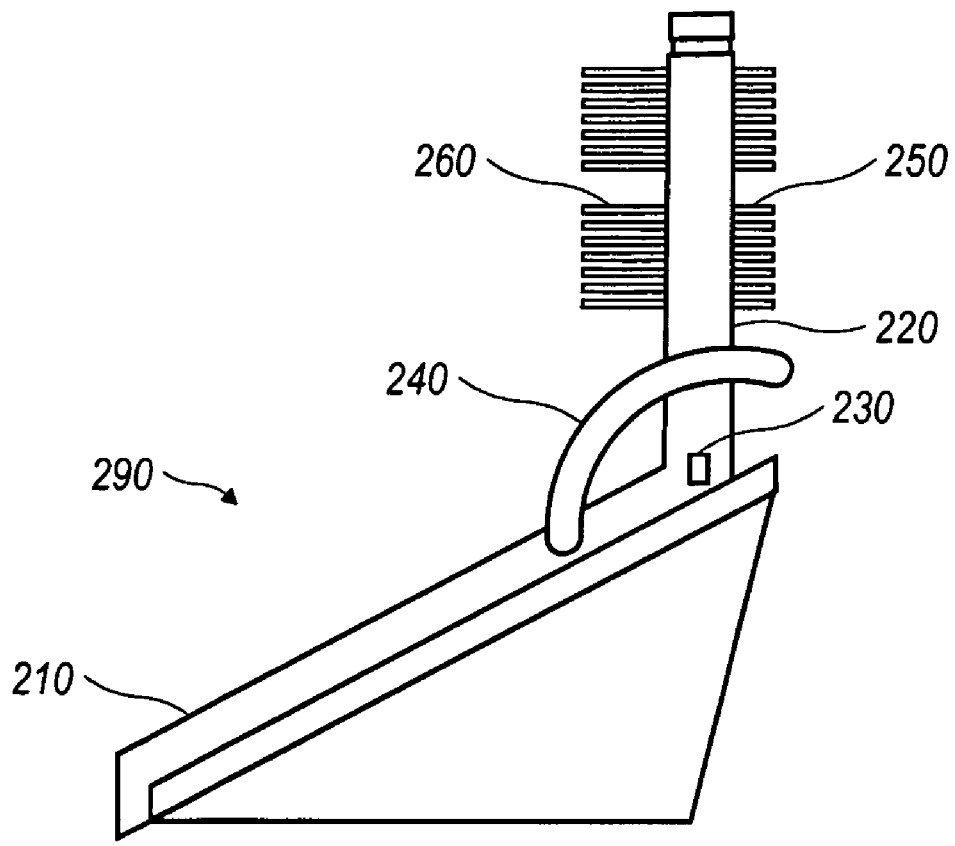
FIG. 2 shows an alignment device according to an exemplary embodiment.

Referring to FIG. 2, an alignment device 290 is shown. Alignment device can be integrated into the microtome or may be an added component, which can be optionally removable from the microtome. Alignment device 290 has a knife holder component 210 connected to a pin alignment component 220 with a hinge 230. It is contemplated that the hinge can couple the knife holder component 210 to the pin alignment component 220 in any configuration such that the pin alignment component is rotatable about an axis extending through hinge 230 while the knife holder component maintains a stationary position on the knife holder. The knife holder component 210 and the pin alignment component 220 can be a single structure or separate structures. In one embodiment, the knife holder component 210 is disposable.

Based in part on the structural properties (e.g., hardness) of the block specimen 130 or a knife profile (e.g., an angle of the knife's edge), the clearance angle of the knife holder component 210 may need to be adjusted to prevent chatter or compression during slicing. As the knife holder component 210 rotates, the pin alignment component 220 may no longer reflect an upright orientation that is parallel to the knife's slicing plane. Accordingly, in order to ensure that the pin alignment component 220 maintains a preferred orientation, the pin alignment component 220 can be adjusted to match the clearance angle of the microtome. An angle indicator 240, which can identify the angle between the knife holder component 210 and the pin alignment component 220, can be used to match the angle between the knife holder component 210 and the pin alignment component 220 to the clearance angle on the microtome, shown by the clearance angle adjustment 180 in FIG. 1.

Pin alignment component 220 has a plurality of front pins 250 extending from a front side and a plurality of rear pins 260 extending from a rear side of the pin alignment component 220. Although front pins 250 and rear pins 260 are illustrated as cylindrical members, it is intended that front pins and rear pins can embody any shape to accomplish their intended purposes. Pins 250 can be coupled to pins 260 so that movement of pins 250 is reflected by movement of pins 260. Pins 250 extending from the front side of the pin alignment component 220 are intended to contact a paraffin block. However, due to the size of the paraffin block or the positioning and angle of the paraffin block, it is understood that not every pin 250 may contact the paraffin block.

Pins 260 extending from the rear of pin alignment component 220 can have indicia such as lines, text (e.g., numbers), color, or other marking to indicate the extension of a pin from the pin alignment component 220. In a configuration where the indicia are viewed by a human eye, the indicia have sufficiently large distinctions to discern each indicia. In one embodiment, the indicia are spaced approximately 0.75 mm to 2.0 mm in length along the pins 260. For example, the indicia can be spaced approximately 1.0 mm apart. In an alternative embodiment where a magnifying lens is used to view the pins, the indicia can be spaced approximately 0.25 mm to 0.75 mm apart. For example, the indicia can be spaced approximately 0.5 mm apart. It is understood that the indicia in these embodiments can be larger or smaller and are not intended to be limited to these exemplary embodiments. In an embodiment where colors are used as the indicia, the colors are compliant with Section 508 of the Rehabilitation Act of 1973 and Rehabilitation Act Amendments of 1998 so that color blind people can distinguish between indicia. In an exemplary embodiment, pins have alternating colors. In another exemplary embodiment, each indicia is a different color. In yet another exemplary embodiment, each indicia has a different pattern. Accordingly, these indicia can allow a user to determine a preferred sample alignment position and repeat or change a sample alignment based on previously predetermined positions. Whether slicing a specimen for the first time or realigning a block specimen that has been removed from a microtome, the indicia can provide a guide to the user as to how to adjust the specimen to obtain a desired slice. Where one pin may be more extended than another pin (e.g., one pin may extend 1 mm and another pin may extend 2 mm), a user can appropriately adjust the angle of the specimen to the desired plane.

Pins 250 and pins 260 can be constructed of any durable material that resists oxidation, such as stainless steel. It is desirable to use a material that can withstand a lot of movement, is highly durable, and does not bend. It may also be desirable to have a material that can withstand high temperature and high pressure, such as those conditions encountered in an autoclave. For use in a cryostat, it may be desirable to use a material that can withstand cold temperatures as well as changes between a room temperature and cold temperature environment.

In an exemplary operation of alignment device 290, when aligning the block specimen with the knife to minimize specimen loss, a user can advance the block forward until it substantially abuts pins 250. Because the block will likely be in a plane differing from the desired slicing plane, pins 250 will extend at different lengths to contact the block. As a result, pins 260 will also extend at different lengths. Indicia on pins 260 provide the user with an indication of the plane of the block specimen and how that plane must be adjusted within the X-, Y-, and Z-planes. The user can calibrate the chuck holding the block so that the pins 260 reflect that the block is positioned in a desired plane.

In one example, the indicia on the pins 260 can be graduated by measurement of extension, such as by increments of 1 millimeter. As such, at a zero position where the block is not contacting the pins 250, pins 260 reflect a zero millimeter movement. Every millimeter (e.g., 1 mm, 2 mm, 3 mm . . . n mm), there is a marker to indicate the extension of the pin 260 from the pin alignment component 220. Before a block specimen is aligned, one pin may indicate an extension of 1 mm, while another pin may indicate an extension of 2 mm. The chuck can be adjusted within the X-, Y-, and Z-planes so that each indicia reflects the same extension. In other words, the angle of the block can be adjusted so that every pin indicates a 1 mm extension. When the indicia shows each pin extending 1 mm, the surface of the block is aligned with the cutting plane of the knife.

Although it is contemplated that a front pin can be the same component as or directly coupled to a rear pin, it may be desirable to utilize at least one class III lever between the front pin and the rear pin in order to amplify the front pin's movement, such that the movement of the rear pin is on a greater scale. In other words, when the front pin moves only a few microns, it may be desirable to reflect this movement as a larger movement on the rear pins for the user's benefit. The resulting magnification of the front pins movement can allow a user to adjust the front pins and view slight movements on a small scale that would be difficult for even a trained technician using conventional methods. By using additional class III levers, as discussed below, the user can observe even greater magnification of the front pin's movement.

Figure 3:
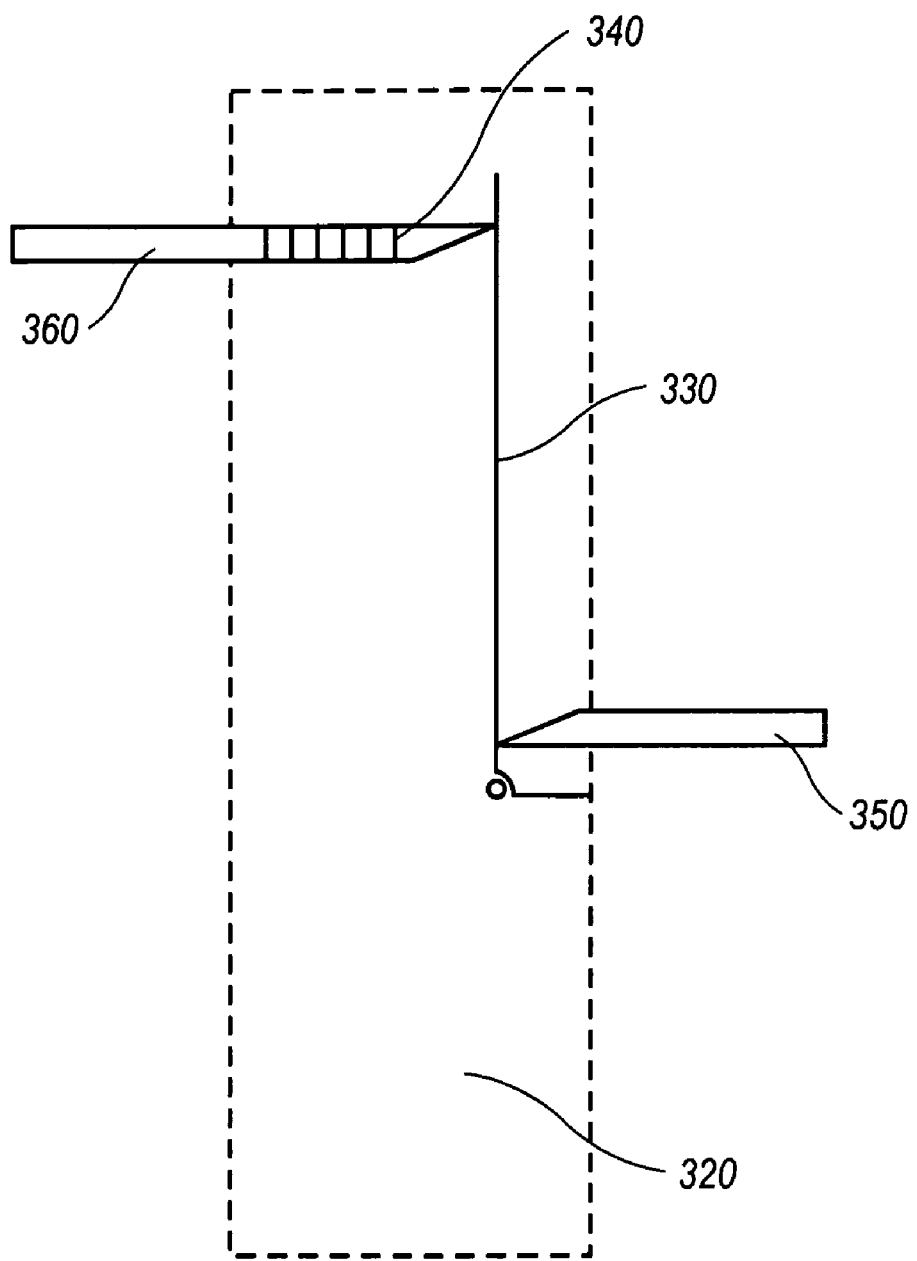
FIG. 3 shows a cross-sectional view of a pin alignment component according to an exemplary embodiment.

Referring to FIG. 3, in an example of how a front pin interacts with a rear pin, a cross-sectional view of a pin alignment component 320 is shown. A front pin 350 extends from the front side of pin alignment component 320 and a rear pin 360 extends from the rear side of pin alignment component 320. Pin 350 contacts with a block specimen, which forces the pin 350 against a lever 330. Lever 330 is designed as a class III lever, discussed in further detail below. Lever 330 then applies pressure to pin 360, causing pin 360 to extend from pin alignment component 320. As described above, pin 360 can have indicia 340 to indicate the extension of the pin 360 from the pin alignment component 320. The indicia 340 may be located on pin 360 between the lever 330 and the edge of the pin alignment component 330. Pin alignment component 320 can be hollowed to provide for movement of lever 330. Lever 330 can be constructed of any durable material and can resist oxidation, such as stainless steel. It is desirable to use a material that can withstand a lot of movement, is highly durable, and does not bend. It may also be desirable to have a material that can withstand high temperature and pressure, such as in an autoclave.

Pins 350, 360 may be slidably engaged to lever 330. Upon a movement of lever 330, which is a slight rotational movement about a fulcrum, a slidable engagement can allow pins 350, 360 to slide in a horizontal direction without substantial vertical forces. Additionally, the slidable engagement can allow pin 360 and lever 330 to return to a starting position when the block is no longer exerting pressure on pin 350.

Referring to FIGS. 4a to 4c, a perspective view of a pin alignment component 400 is shown. Pin alignment component 400 has a plurality of front pins 450 arranged on the front surface and a plurality of rear pins 460 arranged on the rear surface of the pin alignment component 400. This configuration of the pins 450, 460 is merely exemplary and is not intended to be the only configuration or arrangement of pins on a pin alignment component. Additionally, pin alignment component 400 is depicted with a plurality of pins, but pin alignment component 400 can have any number of pins. Employing the exemplary lever depicted in FIG. 3, pin 450 extending from the front side of pin alignment component 400 would have corresponding pin 460 extending from the rear at a different position along the surface of the pin alignment component 400. It is understood that the distance between these pins is dependent upon the length of a lever (not shown in FIG. 4) that can connect the front and rear pins. In this exemplary embodiment, by positioning the pins 450 in a perpendicular manner on the front of pin alignment component 400, the rear of pin alignment component 400 accordingly has pins 460 positioned along the edge. It can be desirable to have a pin configuration, including the number of pins, that can reflect a block angle on different axes such that a microtome user can accurately and precisely determine and adjust the alignment of the block specimen. Pin alignment component 400 can also have a level 430 to adjust the positioning of the pin alignment component 400 on a microtome. Level 430 can assist in orienting the pin alignment component with the clearance angle of the knife on the microtome.

Figure 5A:
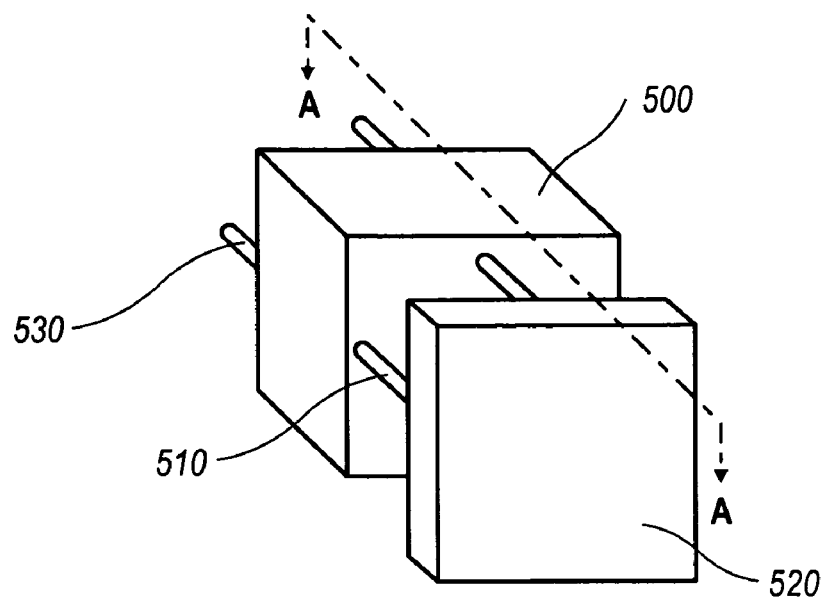
FIGS. 5a to 5b show views of a pin alignment component according to exemplary embodiments.
Figure 5B:
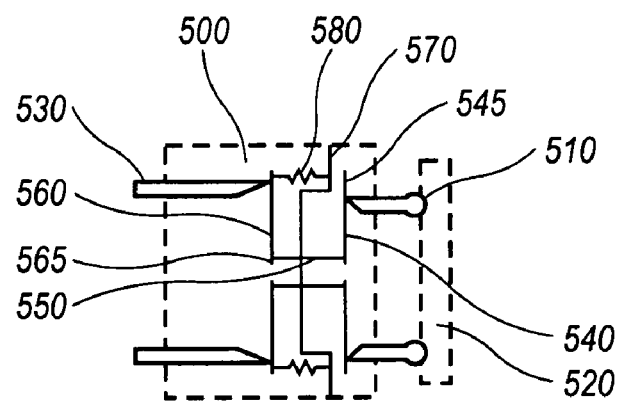

In an alternative embodiment, referring to FIG. 5a and a cross-sectional view through line A-A in FIG. 5b, a pin alignment component 500 can have a plurality of pins 510 extending from a front surface of the pin alignment component to a rear surface of a contact surface component 520. In this embodiment, a front surface of the contact surface component 520 substantially abuts a sample in the microtome. In this exemplary configuration, pins 510 engage the contact surface component 520 with a ball-and-socket, but the pins 510 can have any shape, such as a rectangular shape, that engages the contact surface component 520. Pins 510 can be constructed of any durable material and can resist oxidation, such as stainless steel or plastic. It is desirable to use a material that can withstand a lot of movement and friction, and is highly durable. It may also be desirable to have a material that can withstand high temperature and high pressure, such as in an autoclave.

In order to effectuate a magnified view of the positioning between pins 510, a lever system can be used such that pins 530 extending from a rear of pin alignment component 500 reflect a greater movement than experienced by pins 510. In other words, because pins 510 may have such a small movement in response to a block specimen, as described above, it may be desirable to magnify these movements on pins 530 so an operator can more easily observe these movements. Pins 510 engage a first lever 540 that engages a connecting piece 550 that engages a second lever 560. Second lever 560 actuates pin 530. A barrier 570 is positioned between the first lever 540 and the second lever 560. A spring 580 can be positioned between barrier 570 and lever 560 to allow the lever 560 to reset to a starting position when a force on pin 510 is removed.

Lever 540 has a fulcrum 545, which is positioned approximately 0.5 mm from the contact point of pin 510 to contact surface component 520. Connecting piece 550 is approximately 10 mm from fulcrum 545 on a first end and approximately 0.5 mm from a fulcrum 565 on lever 560. Connecting piece 550 can pass through an aperture on barrier 570 to allow the connecting piece 550 to slide as pressure is applied to lever 540 as well as to keep connecting piece 550 in a proper position. Pin 530 is positioned approximately 10 mm from fulcrum 565. It is understood that these measurements are merely exemplary and can be configured in a variety of dimensions. In one embodiment, a notch in a component is provided to receive an end of another component for enabling the sliding of the components. For example, lever 540 can have a notch to receive pin 510.

As a result of this exemplary configuration, as contact surface component 520 contacts and substantially abuts a block specimen, the surface of contact surface component 520 will adjust within the X-, Y-, and Z-planes to reflect the positioning of the block specimen. Accordingly, each pin 510 will also move to reflect the movement of contact surface component 520. Pin 530 reflects any movement of pin 510. The movement of pin 530, however, is a scaled magnification of the movement of pin 510. Because of the exemplary multiple class III lever configuration, a slight movement by pin 510, even if just a few microns, can be magnified by the movement of each lever. As a result, pin 530 can magnify these slight movements so that the user can observe them with the naked eye. For example, when pin 510 moves 10 µm, pin 530 moves 1 mm. And once the movements are observed on pin 530, the user can adjust and calibrate the positioning of the chuck such that the pins 530 are in substantial alignment with each other, thereby positioning the block in a plane that is in an ideal position relative to the knife. In one example, when one pin 530 extends 1 mm and another pin 530 extends 2 mm, the user can adjust the angles of the chuck so that the block abutting contact surface component 520 causes each pin 530 to extend the same distance, e.g., 1 mm.

When working with ribonucleic acid (RNA), it is desirable to maintain an environment free of ribonuclease (RNase), a nuclease that catalyzes the hydrolysis of RNA. RNases are very common and can be present on hands and/or as airborne dust particles. As a result, when working with a sample, such as a tissue containing RNA, it may be desirable to prepare the sample in an RNase-free environment. In order to achieve this type of sterility, it may require an RNase-free sample and an RNase-free microtome.

In an alternative embodiment, a film or a wrapping, preferably disposable, can be situated over a front surface of a contact surface component. In one exemplary method, the disposable film can be removably attached to the contact surface component by electrostatic forces. By using the film on the contact surface component, the film can act as a barrier between the contact surface component and a block specimen for protection or sterility purposes, such as in an RNase-free environment.

Figure 6A:
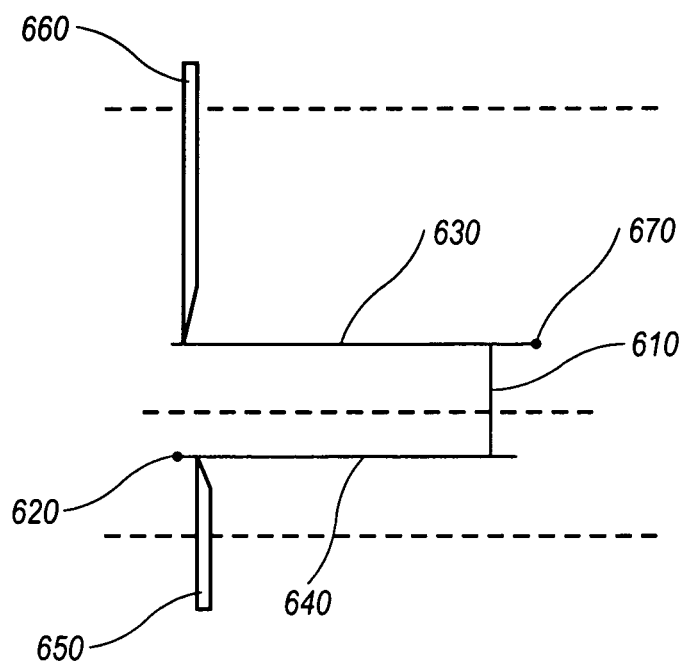
FIGS. 6a and 6b show a cross-sectional view of a lever operation according to an exemplary embodiment.
Figure 6B:
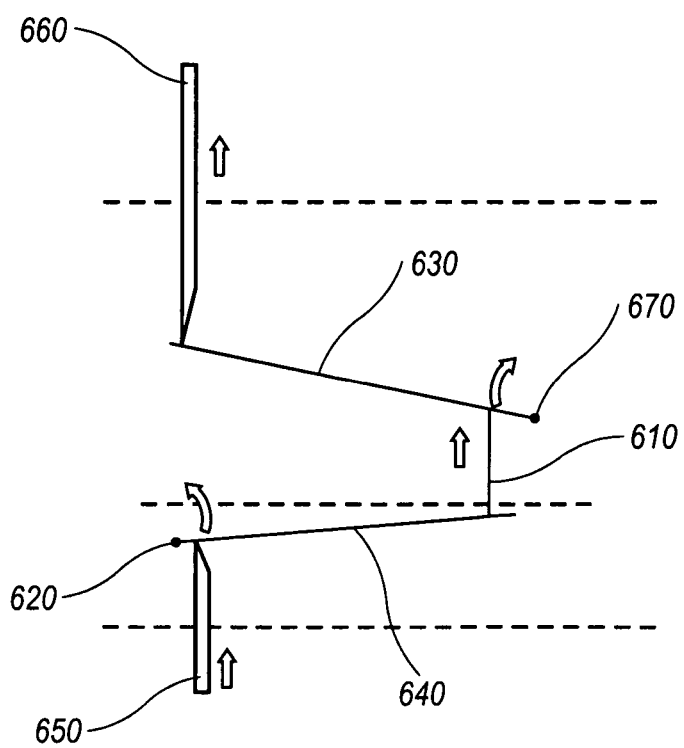

In order to amplify the slight movement of a pin, at least one class III lever can be used, as described herein. Any number of levers can be used between a front pin and a rear pin, whereby adding additional levers increases the amplification of effects on the front pin. Referring to FIGS. 6a and 6b, an exemplary operation of a lever configuration having two class III levers is shown. FIG. 6a shows a pin 650 without any force exerted upon it by a pin alignment component (not shown). In FIG. 6b, using arrows to show the general direction of movement of each component once a force is exerted, pin 650 causes a lever 640 (having a fulcrum 620) to move, which causes a connecting piece 610 to move, which causes a lever 630 (having a fulcrum 670) to move, which causes a pin 660 to move. As a result of this lever configuration, pin 660 can move a greater and more appreciable distance than pin 650. For example, if pin 650 moves a slight distance, even on the scale of microns or nanometers (e.g., 10 µm), the lever configuration can amplify the resulting movement of pin 660 to millimeters (e.g., 1 mm), which may be more appreciable by a human technician.

Figure 7A:
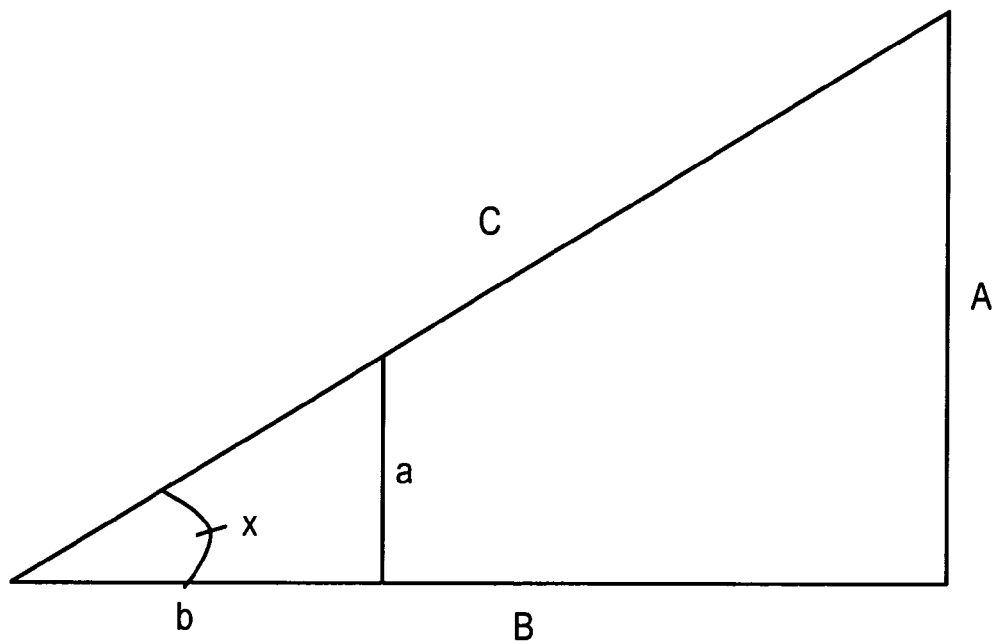
FIGS. 7a to 7d show methods of lever configuration according exemplary embodiments.
Figure 7B:
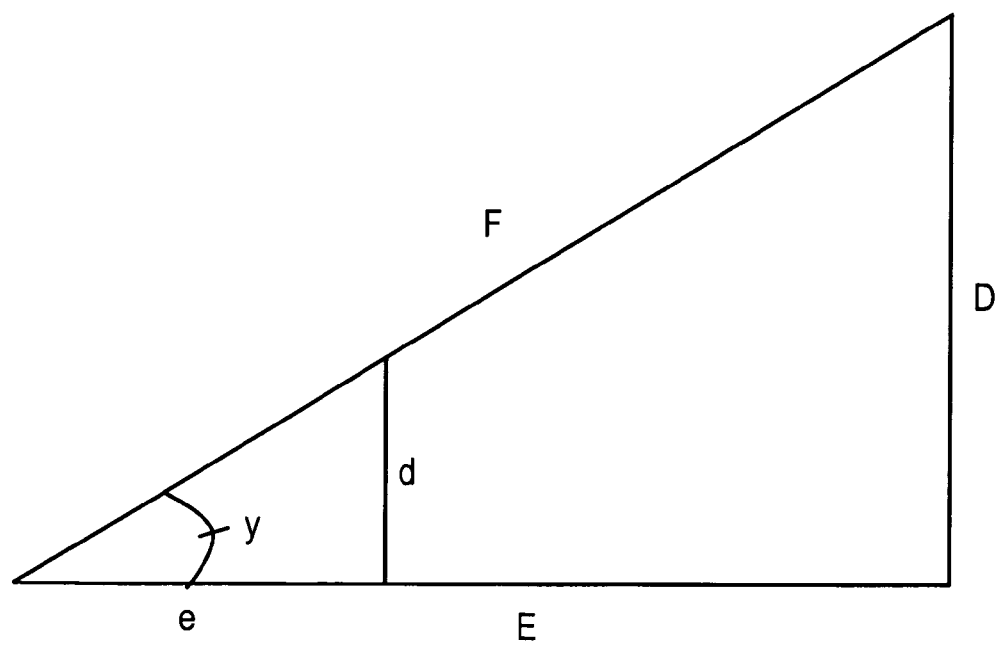
Figure 7C:
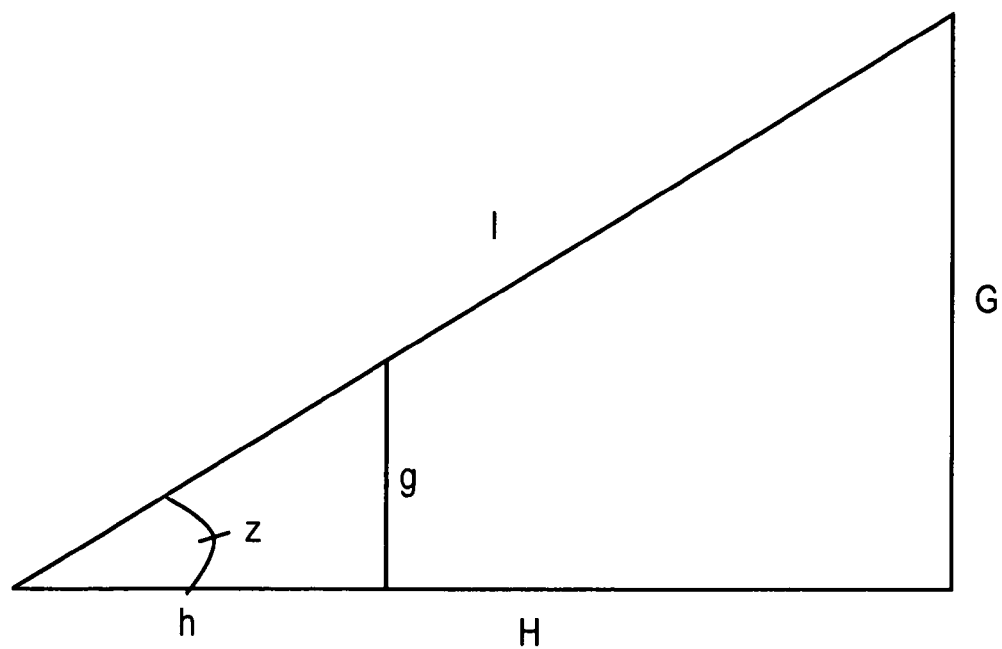

Referring to FIGS. 7a to 7c, an exemplary method for determining a lever configuration is shown. In this exemplary lever configuration, there are three components: a fulcrum, an effort, and a resistance. In the exemplary embodiment shown in FIG. 5b, an exemplary fulcrum is fulcrum 545, an exemplary effort is pin 510, and an exemplary resistance is connecting piece 550. In this exemplary embodiment, the fulcrum is the same as a pivot point, the point where the resistance is stationarily fixed and allows the resistance to move about that point. Pressure is applied to the effort, which contacts the resistance near the fulcrum.

An exemplary method is provided to calculate the point at which the effort should contact the resistance as measured from the fulcrum. In this example, when the effort is moved 5 μm, the resistance, which is 20000 μm from the fulcrum, is to be moved 2000 μm. Referring to FIG. 7a, an angle x is to be determined where the desired movement A is 2000 and the distance between the resistance and the fulcrum B is 20000. Calculating Tan(x)=A/B, x is approximately 5.71059 degrees. Next, the distance between the fulcrum and the effort b, is to be determined. Calculating Tan(x)=a/b, where x is 5.71059 and a is 5, the distance b is about 50 μm. Thus, the effort should contact the resistance at about 50 μm from the fulcrum.

In a configuration, for example, where 50 μm may be too close to locate the effort in relation to the fulcrum, it may be desirable to position the effort at 0.5 mm or 500 μm from the fulcrum. Referring to FIG. 7b, an exemplary method is shown for determining the distance E of a resistance D from a fulcrum to cause a 5 μm change in an effort that results in a 2000 mm change in the resistance. In order to find an angle y, Tan(y)=d/e, where desired change d is 5 and desirable effort position e is 500. So angle y is 0.57294 degrees. Using angle y, length E is calculated by Tan(y)=D/E, where D is 20000, so length E is approximately 2,000,000 μm or 200 cm. As a result, this length may be too big to fit into the device.

Because positioning the effort 0.5 mm from the fulcrum may require too much length for the resistance, two levers can be used. A fold increase p is to be calculated for each lever. So a 5 μm change in the effort causes a 2000 μm change in the resistance, so $5p^2=2000$. The fold increase p is squared because one lever acting on another lever causes an exponential change, not an additive change. As a result, p is 20.

Assuming the effort can be positioned 500 μm from the fulcrum, a first lever with a 20 fold change in a 5 μm effort would cause a 100 μm change in the resistance. Calculating Tan(y)=d/e, where d is 5 and e is 500, the angle y is 0.57294 degrees. However, because D is 100, then Tan(y)=D/E, where y is 0.57294, then E is approximately 10,000 μm or 1 cm.

Referring to FIG. 7c, the second lever would move 2000 μm, so length D equals length g, because the resistance from the first lever has become the effort of the second lever. Calculating Tan(z)=g/h, where length g is 100 and length h is 500, z equals 11.30993 degrees. The length H should correspond to the length E of the first lever. Calculating Tan(z)=G/H, where z is 11.30993 and G is 2000, H is approximately 10,000 μm or 1 cm, as calculated above with length E. In this example, there is a 20-fold increase from the first arm from 5 μm to 100 μm, and a 20-fold increase from 100 μm to 2000 μm.

Figure 7D:
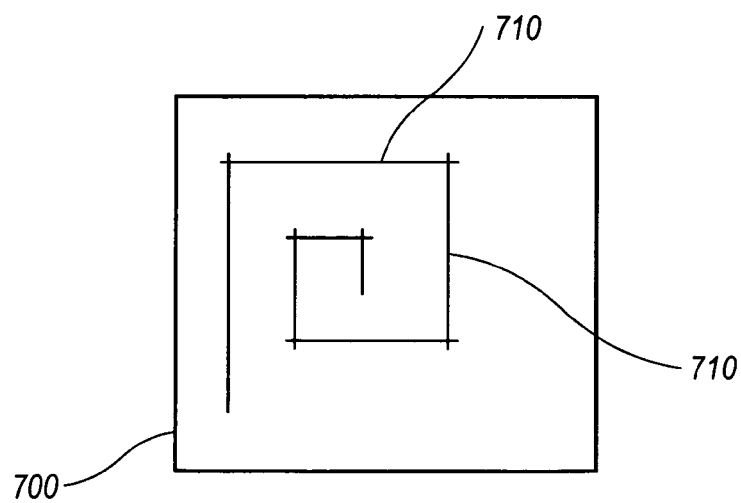

As described above, in an exemplary embodiment, referring to FIG. 7d, a pin alignment component 700 can have a plurality of levers 710 (using efforts and resistances) to amplify the effort's movement, which translates into a larger movement of the resistance. In this embodiment, a series of class III levers 710 are shown from a view of a front face of the pin alignment component 700 for only a single pin. It is understood that pin alignment component 700 has sufficient depth to accommodate these levers for each pin. It is also understood that each pin can have any number of levers.

Additionally, the spiral configuration shown is intended to be merely exemplary. A configuration having a plurality of levers can also be configured to use less space within the pin alignment component, such as the exemplary embodiment having two class III levers shown in FIGS. 6a and 6b. This exemplary embodiment may be desirable for more precise alignment of a microtome knife with a sample. Also, in this exemplary embodiment, a digital display of pin movement may be used, as described below with respect to FIG. 9.

Figure 8:
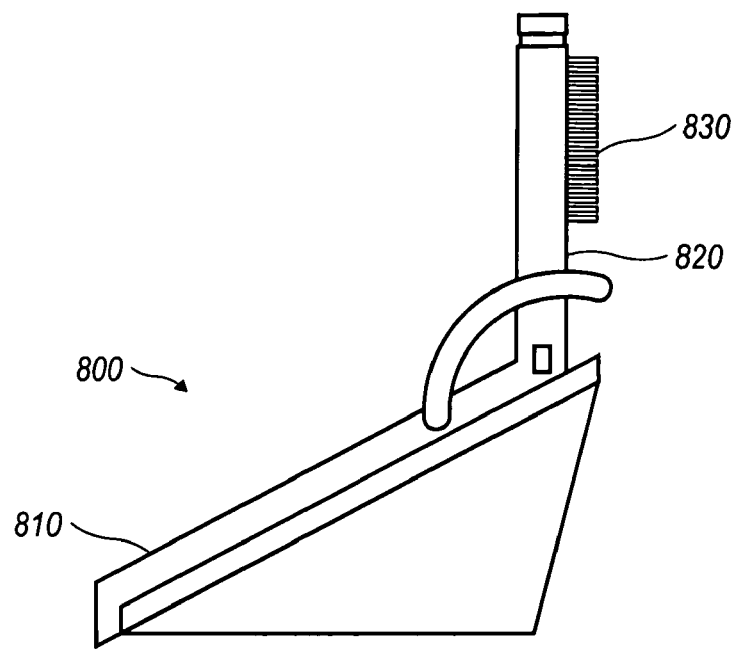
FIG. 8 shows an alignment device having a brush according to an exemplary embodiment.

In yet another alternative embodiment, referring to FIG. 8, an alignment device 800 is shown. Alignment device 800 has a knife holder component 810 connected to an alignment component 820. A plurality of bristles 830 are positioned on a front surface of the alignment component 820 to substantially contact a block specimen. Bristles 830 can be arranged in a rectangle, a cross, at least one horizontal line, at least one vertical line, or any other configuration. In one exemplary embodiment, an outer perimeter of the bristles is approximately the size of a sample. By observing the deflection of the bristles 830, an operator can determine how the bristles 830 are contacting the block specimen. In other words, if a block specimen causes a region of bristles 830 to deflect more, the corresponding region of the block specimen is angled closer to the alignment component 820. In that instance, the block specimen is not in alignment with the cutting plane of the knife. The block specimen can be considered aligned once all bristles 830 that contact the block specimen incur the same amount of deflection. In one exemplary embodiment, the bristles 830 can be disposable.

Figure 9:
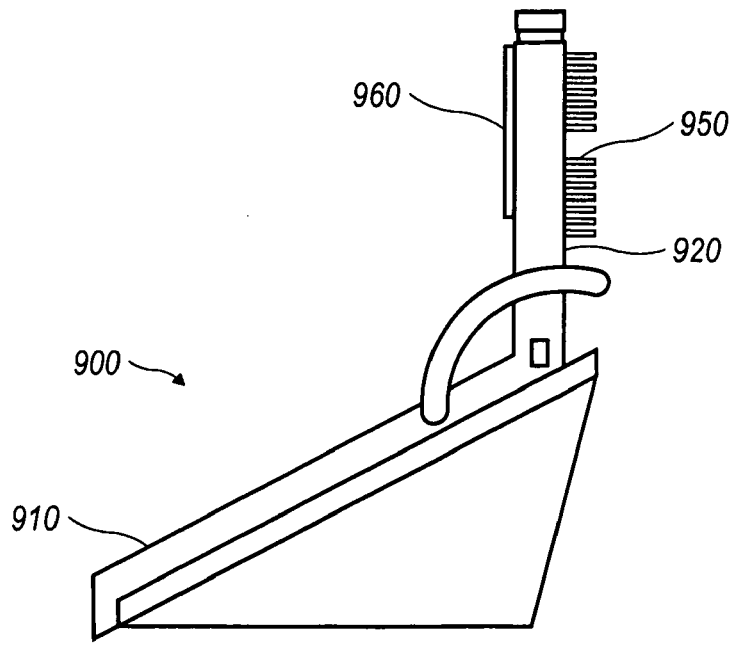
FIG. 9 shows an alignment device having a digital display according to an exemplary embodiment.

In another embodiment, referring to FIG. 9, an alignment device 900 is shown having a knife holder component 910 connected to a pin alignment component 920. In this exemplary embodiment, pin alignment component 920 has a plurality of pins 950 extending from a front side of the pin alignment component 920, as described in the exemplary embodiment in FIG. 2. However, it is understood that the embodiment described in FIG. 9 is not limited to the embodiment described in FIG. 2. Pin alignment component 920 has a digital display 960, such as a liquid crystal display, on a rear surface of pin alignment component 920. The digital display 960 can provide any number of numerical or visual indications, including a numerical representation of an extension of at least one of the pins 950. Alternatively, the digital display 960 can be positioned other than on the pin alignment component 920. In one exemplary embodiment, the pins 950 are pressure sensitive.

The alignment devices described in any of the above exemplary embodiments can be integrated into the microtome or can be an added component. In either configuration, any or all components of the alignment device can be disposable. However, the disposable nature of a component is not intended to be limited to a single use or any other particular number of uses.

The embodiments described above are intended to be exemplary. One skilled in the art recognizes that numerous alternative components and embodiments that may be substituted for the particular examples described herein and still fall within the scope of the invention.

What is claimed is:

1. A device for aligning a block specimen in a microtome, the device comprising:
   a knife holder component removably attached to a knife holder of the microtome;
   a pin alignment component extending vertically from the knife holder component in a direction substantially parallel to the block specimen, the pin alignment component comprising:

a plurality of front pins extending from a front surface of the pin alignment component configured to slide in response to an angle of the block specimen; and a plurality of rear pins extending from a rear surface of the pin alignment component and coupled to the front pins; and an angle indicator indicating an angle between the knife holder component and the pin alignment component;

wherein the rear pins are configured to indicate the extension of the front pins from the pin alignment component.

2. The device according to claim 1, wherein the rear pins have indicia of at least two colors.

3. The device according to claim 1, wherein the rear pins have alphabetic or numeric indicia.

4. The device according to claim 1, wherein the front pins are arranged along a horizontal axis and a vertical axis of the front surface of the pin alignment component.

5. The device according to claim 1, wherein the rear pins are arranged substantially along the perimeter of the rear surface of the pin alignment component.

6. The device according to claim 1, further comprising a contact surface component that engages the front pins, wherein the contact surface component is configured to contact the block specimen.

7. The device according to claim 6, further comprising a film extending across a front surface of the contact surface component.

8. The device according to claim 7, wherein the film removably attaches using electrostatic forces.

9. A device for aligning a block specimen in a microtome, the device comprising:

a knife holder component removably attached to a knife holder of the microtome;

a pin alignment component extending vertically from the knife holder component in a direction substantially parallel to the block specimen, the pin alignment component comprising:

a plurality of front pins extending from a front surface of the pin alignment component configured to slide in response to an angle of the block specimen; and a plurality of rear pins extending from a rear surface of the pin alignment component and coupled to the front pins; and at least one lever for coupling a front pin with a rear pin;

wherein the rear pins are configured to indicate the extension of the front pins from the pin alignment component.

10. The device according to claim 9, further comprising a spring configured to allow the at least one lever to reset to a starting position.

11. The device according to claim 9, wherein the at least one lever comprises:

a first lever configured to move when a force is applied to a front pin:

a second lever configured to move when the first lever moves; and a third lever configured to move when the second lever moves and configured to move a rear pin.

* * * * *